United States Patent
Augostino et al.

(10) Patent No.: US 7,051,451 B2
(45) Date of Patent: May 30, 2006

(54) FACET JOINT PROSTHESIS MEASUREMENT AND IMPLANT TOOLS

(75) Inventors: Teena M. Augostino, Redmond, WA (US); Richard J. Broman, Monroe, WA (US); Leonard Tokish, Jr., Issaquah, WA (US)

(73) Assignee: Archus Orthopedics, Inc., Redmond, WA (US)

( * ) Notice: Subject to any disclaimer, the term of this patent is extended or adjusted under 35 U.S.C. 154(b) by 0 days.

(21) Appl. No.: 10/831,651

(22) Filed: Apr. 22, 2004

(65) Prior Publication Data

US 2005/0235508 A1    Oct. 27, 2005

(51) Int. Cl.
  *G01B 5/24* (2006.01)
  *A61B 17/56* (2006.01)

(52) U.S. Cl. .................. 33/512; 33/1 N; 606/102

(58) Field of Classification Search ............... 606/102, 606/61, 73; 623/912, 914; 33/511, 512, 33/513, 514, 534, 538, 1 N
See application file for complete search history.

(56) References Cited

U.S. PATENT DOCUMENTS

| | | | | |
|---|---|---|---|---|
| 1,308,451 A | * | 7/1919 | Schachat | 33/418 |
| 2,930,133 A | * | 3/1960 | Thompson | 33/512 |
| 2,959,861 A | * | 11/1960 | Stromquist | 33/419 |
| 3,867,728 A | | 2/1975 | Stubstad et al. | |
| 3,875,595 A | | 4/1975 | Froning | |
| 4,123,848 A | * | 11/1978 | Emmerich et al. | 33/534 |
| 4,271,836 A | * | 6/1981 | Bacal et al. | 606/61 |
| 4,349,921 A | | 9/1982 | Kuntz | |
| 4,710,075 A | * | 12/1987 | Davison | 408/202 |
| 4,759,769 A | | 7/1988 | Hedman et al. | |
| 4,772,287 A | | 9/1988 | Ray et al. | |
| 4,863,477 A | | 9/1989 | Monson | |
| 4,904,260 A | | 2/1990 | Ray et al. | |
| 4,911,718 A | | 3/1990 | Lee et al. | |
| 4,955,916 A | | 9/1990 | Carignan et al. | |
| 4,987,904 A | * | 1/1991 | Wilson | 600/587 |
| 5,015,255 A | | 5/1991 | Kuslich | |
| 5,047,055 A | | 9/1991 | Bao et al. | |

(Continued)

FOREIGN PATENT DOCUMENTS

DE    10135771 A1    2/2003

(Continued)

OTHER PUBLICATIONS

Gunzberg, R. et al., "Arthroplasty of the Spine". Berlin; New York; Springer, 2004.

(Continued)

*Primary Examiner*—R. Alexander Smith
(74) *Attorney, Agent, or Firm*—Wilson Sonsini Goodrich & Rosati

(57) ABSTRACT

The present invention provides tools and methods designed to aid in the placement of facet joint prosthesis at virtually all spinal levels. One aspect of the present invention is a measurement tool for installing a cephalad facet joint prosthesis including a fixation measurement element and a support arm element. This measurement tool assists in the selection and/or configuration of a cephalad facet joint prosthesis for implantation in a patient. Another aspect is a measurement tool for installing a caudal facet joint prosthesis including a stem element and a trial caudal bearing surface element. This measurement tool assists in the selection and/or configuration of a caudal facet joint prosthesis for implantation in a patient. Yet another aspect is a measurement tool holder including a measurement surface connected to a holder element. This tool holder assists in determining the measurements obtained with the caudal facet joint prosthesis measurement tool.

38 Claims, 15 Drawing Sheets

U.S. PATENT DOCUMENTS

| | | |
|---|---|---|
| 5,062,845 A | 11/1991 | Kuslich et al. |
| 5,070,623 A * | 12/1991 | Barnes ................... 33/807 |
| 5,071,437 A | 12/1991 | Steffee |
| 5,092,866 A | 3/1992 | Breard et al. |
| 5,147,404 A | 9/1992 | Downey |
| 5,171,280 A | 12/1992 | Baumgartner |
| 5,192,326 A | 3/1993 | Bao et al. |
| 5,258,031 A | 11/1993 | Salib et al. |
| 5,300,073 A | 4/1994 | Ray et al. |
| 5,303,480 A * | 4/1994 | Chek ...................... 33/512 |
| 5,306,308 A | 4/1994 | Gross et al. |
| 5,306,309 A | 4/1994 | Wagner et al. |
| 5,312,409 A | 5/1994 | McLaughlin et al. |
| 5,314,429 A * | 5/1994 | Goble ..................... 606/96 |
| 5,329,933 A * | 7/1994 | Graf ....................... 600/594 |
| 5,350,380 A | 9/1994 | Goble et al. |
| 5,370,697 A | 12/1994 | Baumgartner |
| 5,401,269 A | 3/1995 | Buttner-Janz et al. |
| 5,415,661 A | 5/1995 | Holmes |
| 5,425,773 A | 6/1995 | Boyd et al. |
| 5,437,672 A | 8/1995 | Alleyne |
| 5,445,639 A | 8/1995 | Kuslich et al. |
| 5,458,642 A | 10/1995 | Beer et al. |
| 5,458,643 A | 10/1995 | Oka et al. |
| 5,491,882 A | 2/1996 | Walston et al. |
| 5,507,823 A | 4/1996 | Walston et al. |
| 5,514,180 A | 5/1996 | Heggeness et al. |
| 5,527,312 A | 6/1996 | Ray |
| 5,534,028 A | 7/1996 | Bao et al. |
| 5,534,030 A | 7/1996 | Navarro et al. |
| 5,545,229 A | 8/1996 | Parsons et al. |
| 5,556,431 A | 9/1996 | Buttner-Janz |
| 5,562,738 A | 10/1996 | Boyd et al. |
| 5,571,189 A | 11/1996 | Kuslich |
| 5,571,191 A | 11/1996 | Fitz |
| 5,577,995 A | 11/1996 | Walker et al. |
| 5,587,695 A | 12/1996 | Warmerdam |
| 5,603,713 A | 2/1997 | Aust et al. |
| 5,645,597 A | 7/1997 | Krapiva |
| 5,649,930 A | 7/1997 | Kertzner |
| 5,653,762 A | 8/1997 | Pisharodi |
| 5,658,338 A | 8/1997 | Tullos et al. |
| 5,662,651 A | 9/1997 | Tornier et al. |
| 5,674,295 A | 10/1997 | Ray et al. |
| 5,674,296 A | 10/1997 | Bryan et al. |
| 5,676,701 A | 10/1997 | Yuan et al. |
| 5,678,317 A * | 10/1997 | Stefanakos ................ 33/512 |
| 5,683,391 A | 11/1997 | Boyd |
| 5,683,464 A | 11/1997 | Wagner et al. |
| 5,700,268 A * | 12/1997 | Bertin ...................... 606/102 |
| 5,702,450 A | 12/1997 | Bisserie |
| 5,704,941 A | 1/1998 | Jacober et al. |
| 5,716,415 A | 2/1998 | Steffee |
| 5,741,261 A | 4/1998 | Moskovitz et al. |
| 5,824,093 A | 10/1998 | Ray et al. |
| 5,824,094 A | 10/1998 | Serhan et al. |
| 5,836,948 A | 11/1998 | Zucherman et al. |
| 5,860,977 A | 1/1999 | Zucherman et al. |
| 5,865,846 A | 2/1999 | Bryan et al. |
| 5,868,745 A | 2/1999 | Alleyne |
| 5,879,396 A | 3/1999 | Walston et al. |
| 5,885,286 A * | 3/1999 | Sherman et al. ............ 606/61 |
| 5,893,889 A | 4/1999 | Harrington |
| RE36,221 E | 6/1999 | Breard et al. |
| 6,001,130 A | 12/1999 | Bryan et al. |
| 6,014,588 A | 1/2000 | Fitz |
| 6,019,792 A | 2/2000 | Cauthen |
| 6,039,763 A | 3/2000 | Shelokov |
| 6,048,342 A | 4/2000 | Zucherman et al. |
| 6,053,917 A * | 4/2000 | Sherman et al. ............ 606/61 |
| 6,063,121 A | 5/2000 | Xavier et al. |
| 6,066,325 A | 5/2000 | Wallace et al. |
| 6,068,630 A | 5/2000 | Zucherman et al. |
| RE36,758 E | 6/2000 | Fitz |
| 6,080,157 A | 6/2000 | Cathro et al. |
| 6,113,637 A | 9/2000 | Gill et al. |
| 6,120,510 A * | 9/2000 | Albrektsson et al. ......... 606/96 |
| 6,132,464 A | 10/2000 | Martin |
| 6,132,465 A | 10/2000 | Ray et al. |
| 6,193,724 B1 * | 2/2001 | Chan ....................... 606/102 |
| 6,193,758 B1 * | 2/2001 | Huebner ................... 623/19.14 |
| 6,200,322 B1 | 3/2001 | Branch et al. |
| 6,293,949 B1 | 9/2001 | Justis et al. |
| 6,302,890 B1 * | 10/2001 | Leone, Jr. ................. 606/91 |
| 6,361,506 B1 * | 3/2002 | Saenger et al. ............. 600/587 |
| 6,419,703 B1 | 7/2002 | Fallin et al. |
| 6,514,253 B1 | 2/2003 | Yao |
| 6,565,605 B1 | 5/2003 | Goble et al. |
| 6,579,319 B1 | 6/2003 | Goble et al. |
| 6,610,091 B1 | 8/2003 | Reiley |
| 6,632,226 B1 * | 10/2003 | Chan ....................... 606/102 |
| 6,638,281 B1 * | 10/2003 | Gorek ..................... 606/96 |
| 6,648,891 B1 * | 11/2003 | Kim ........................ 606/69 |
| 6,669,729 B1 | 12/2003 | Chin |
| 6,712,818 B1 * | 3/2004 | Michelson ................. 606/61 |
| 6,712,849 B1 | 3/2004 | Re et al. |
| 6,761,720 B1 | 7/2004 | Senegas |
| 2001/0012938 A1 | 8/2001 | Zucherman et al. |
| 2001/0020170 A1 | 9/2001 | Zucherman et al. |
| 2002/0029039 A1 | 3/2002 | Zucherman et al. |
| 2002/0151895 A1 | 10/2002 | Soboleski et al. |
| 2003/0181914 A1 | 9/2003 | Johnson et al. |
| 2004/0059429 A1 | 3/2004 | Amin et al. |
| 2004/0116927 A1 | 6/2004 | Graf |
| 2004/0127989 A1 | 7/2004 | Dooris et al. |
| 2004/0143264 A1 | 7/2004 | McAfee |
| 2005/0049705 A1 | 3/2005 | Hale et al. |
| 2005/0080428 A1 * | 4/2005 | White ...................... 606/102 |
| 2005/0085912 A1 | 4/2005 | Amin et al. |
| 2005/0102028 A1 | 5/2005 | Amin et al. |
| 2005/0187560 A1 * | 8/2005 | Dietzel et al. .............. 606/102 |
| 2005/0192589 A1 * | 9/2005 | Raymond et al. ............ 606/99 |
| 2005/0273167 A1 * | 12/2005 | Triplett et al. ............. 623/17.11 |

FOREIGN PATENT DOCUMENTS

| | | |
|---|---|---|
| EP | 1254639 A1 | 11/2002 |
| FR | 2726459 | 5/1996 |
| FR | 2749155 | 12/1997 |
| FR | 2844180 | 3/2004 |
| IE | S970323 | 6/1998 |
| JP | 10179622 A2 | 7/1998 |
| WO | WO 95/05783 A1 | 3/1995 |
| WO | WO 98/48717 A1 | 11/1998 |
| WO | WO 98/56301 A1 | 12/1998 |
| WO | WO 99/05995 A1 | 2/1999 |
| WO | WO 99/23963 A1 | 5/1999 |
| WO | WO 99/60957 A1 | 12/1999 |
| WO | WO 99/65412 A1 | 12/1999 |
| WO | WO 00/38582 A1 | 7/2000 |
| WO | WO 00/62684 A1 | 10/2000 |
| WO | WO 01/30248 A1 | 5/2001 |
| WO | WO 01/97721 A2 | 12/2001 |
| WO | WO 02/089712 A1 | 11/2002 |
| WO | WO 03/020143 A1 | 3/2003 |
| WO | WO 03/101350 A1 | 12/2003 |
| WO | WO 2004/071358 A1 | 8/2004 |
| WO | WO 2004/103227 A1 | 12/2004 |
| WO | WO 2004/103228 A1 | 12/2004 |

OTHER PUBLICATIONS

Sacher, R. Brochure for presentation at MedTech Insight Conference (Oct. 31, 2003) Boston, MA.

Goh, JC et al., "Influence of PLIF cage size on lumbar spine stability", *Spine*, (Jan. 2000), 25(1) Medline abstract (one page).

Head, WC, "Wagner surface replacement arthroplasty of the hip. Analysis of fourteen failures in forty-one hips", *J Bone Joint Surg. Am.*, (Mar. 1981) 63(3), Medline abstract (one page).

Khoo, LT et al., "A biomechanical analysis of the effects of lumbar fusion on the adjacent vertebral motion segment", Proceedings of the 2000 Annual Meeting of the North American Spine Society, New Orleans.

Kotani, Y. et al., "The effects of spinal fixation and destabilization on the biomechanical and histologic properties of spinal ligaments. An in vivo study.", *Spine*, (Mar. 15, 1998) 23(6), Medline abstract (2 pages).

LeMaire, JP et al., "Intervertebral disc prosthesis: results and prospects for the year 2000", *Clinical Orthopaedics and Related Research*, No. 337, pp. 64-76.

Nagata, H. et al., "The effects of immobilization of long segments of the spine on the adjacent and distal facet force and lumbrosacral motion", *Spine*, (Dec. 1993), 18(16):2471-2479, (9 pages).

Nibu, K. et al., "Multidirectional stabilizing potential of BAK interbody spinal fusion system for anterior surgery [see comments]", *J Spinal Discord*, (Aug. 1997), 10(4), Medline abstract (one page).

Tsantrizos, A. et al., "Segmental stability and compressive strength of posterior lumbar interbody fusion implants", *Spine*, (Aug. 1, 2000) 25(15), Medline abstract (one page).

\* cited by examiner

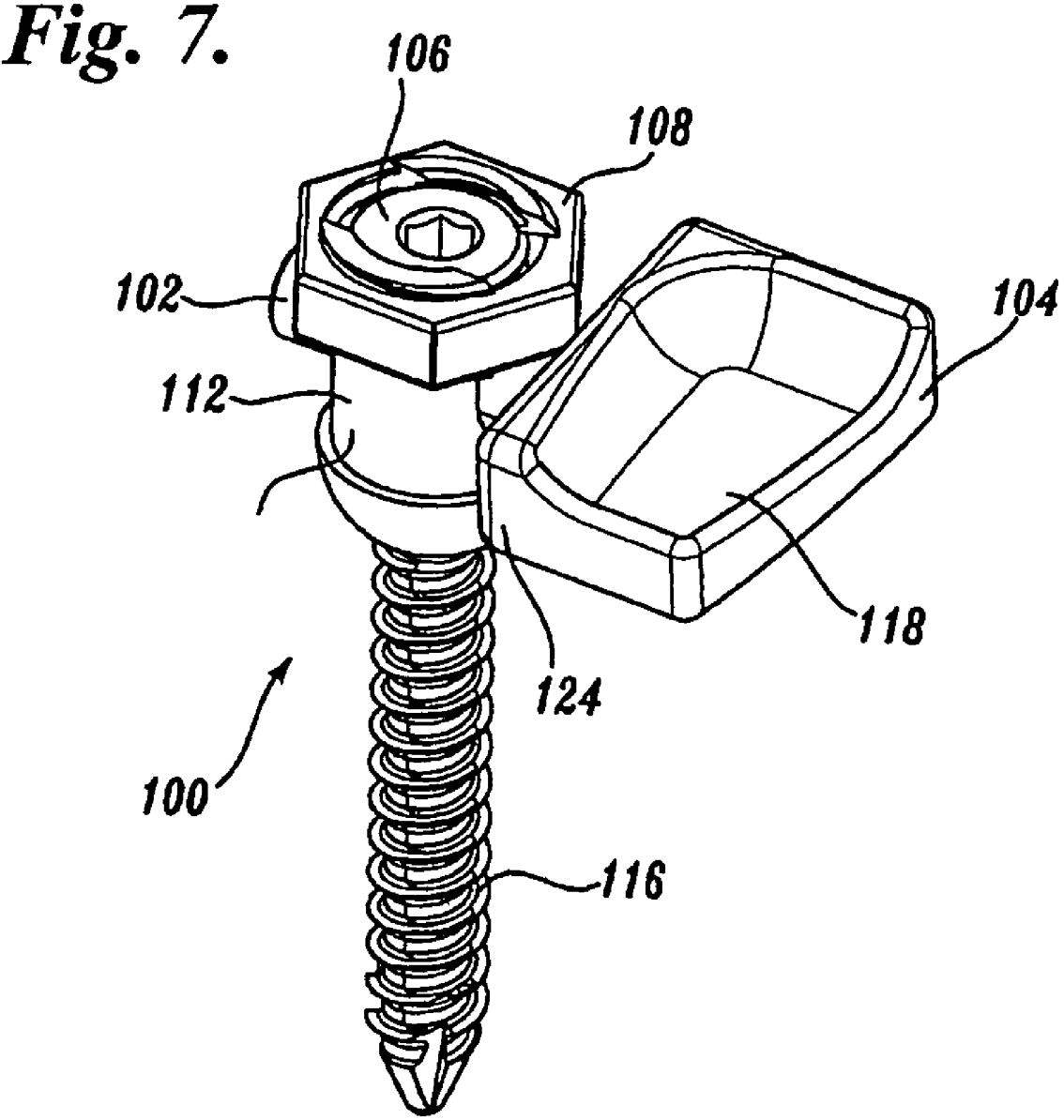

FACET JOINT PROSTHESIS MEASUREMENT AND IMPLANT TOOLS

FIELD OF THE INVENTION

This invention relates to prostheses, systems, and methods for treating various types of spinal pathologies, and in particular relates to the sizing and attachment of prostheses to spinal vertebrae.

BACKGROUND OF THE INVENTION

The human spinal column 10, as shown in FIG. 1, is comprised of a series of thirty-three stacked vertebrae 12 divided into five regions. The cervical region includes seven vertebrae, known as C1–C7. The thoracic region includes twelve vertebrae, known as T1–T12. The lumbar region contains five vertebrae, known as L1–L5. The sacral region is comprised of five vertebrae, known as S1–S5, while the coccygeal region contains four vertebrae, known as Co1–Co4.

FIG. 2 depicts a superior plan view of a normal human lumbar vertebra 12. Although human lumbar vertebrae vary somewhat according to location, they share many common features. Each vertebra 12 includes a vertebral body 14. Two short bones, the pedicles 16, extend backward from each side of the vertebral body 14 to form a vertebral arch 18.

At the posterior end of each pedicle 16, the vertebral arch 18 flares out into broad plates of bone known as the laminae 20. The laminae 20 fuse with each other to form a spinous process 22. The spinous process 22 serves for muscle and ligamentous attachment. A smooth transition from the pedicles 16 to the laminae 20 is interrupted by the formation of a series of processes.

Two transverse processes 24 thrust out laterally on each side from the junction of the pedicle 16 with the lamina 20. The transverse processes 24 serve as levers for the attachment of muscles to the vertebrae 12. Four articular processes, two superior 26 and two inferior 28, also rise from the junctions of the pedicles 16 and the laminae 20. The superior articular processes 26 are sharp oval plates of bone rising upward on each side of the vertebrae, while the inferior processes 28 are oval plates of bone that jut downward on each side.

The superior and inferior articular processes 26 and 28 each have a natural bony structure known as a facet. The superior articular facet 30 faces upward, while the inferior articular facet 31 (see FIG. 3) faces downward. When adjacent vertebrae 12 are aligned, the facets 30 and 31, capped with a smooth articular cartilage, interlock to form a facet joint 32, also known as a zygapophyseal joint.

The facet joint 32 is composed of a superior half and an inferior half. The superior half is formed by the vertebral level below the joint 32, and the inferior half is formed by the vertebral level above the joint 32. For example, in the L4–L5 facet joint, the superior half of the joint 32 is formed by bony structure on the L5 vertebra (i.e., a superior articular surface and supporting bone 26 on the L5 vertebra), and the inferior half of the joint 32 is formed by bony structure on the L4 vertebra (i.e., an inferior articular surface and supporting bone 28 on the L4 vertebra).

An intervertebral disc 34 between each adjacent vertebrae 12 permits gliding movement between the vertebrae 12. The structure and alignment of the vertebrae 12 thus permit a range of movement of the vertebrae 12 relative to each other.

Back pain, particularly in the "small of the back" or lumbosacral (L4–S1) region, is a common ailment. In many cases, the pain severely limits a person's functional ability and quality of life. Such pain can result from a variety of spinal pathologies.

Through disease or injury, the laminae, spinous process, articular processes, or facets of one or more vertebral bodies can become damaged, such that the vertebrae no longer articulate or properly align with each other. This can result in an undesired anatomy, loss of mobility, and pain or discomfort.

For example, the vertebral facet joints can be damaged by either traumatic injury or by various disease processes. These disease processes include osteoarthritis, ankylosing spondylolysis, and degenerative spondylolisthesis. The damage to the facet joints often results in pressure on nerves, also called "pinched" nerves, or nerve compression or impingement. The result is pain, misaligned anatomy, and a corresponding loss of mobility. Pressure on nerves can also occur without facet joint pathology, e.g., a herniated disc.

One type of conventional treatment of facet joint pathology is spinal stabilization, also known as intervertebral stabilization. Intervertebral stabilization prevents relative motion between the vertebrae. By preventing movement, pain can be reduced. Stabilization can be accomplished by various methods.

One method of stabilization is spinal fusion. Another method of stabilization is fixation of any number of vertebrae to stabilize and prevent movement of the vertebrae. Another type of conventional treatment is decompressive laminectomy. This procedure involves excision of some or all of the laminae to relieve compression of nerves.

These traditional treatments are subject to a variety of limitations and varying success rates. None of the described treatments, however, puts the spine in proper alignment or returns the spine to a desired anatomy. In addition, stabilization techniques, by holding the vertebrae in a fixed position, permanently limit a person's mobility.

Artificial facet joint prostheses have been proposed as an alternative to spinal fusion. Examples of such prostheses may be found in U.S. Pat. No. 6,610,091; U.S. Patent Appl. Publ. No. 2002/0123806 A1; U.S. Patent Appl. Publ. No. 2003/0028250 A1; and U.S. patent application Ser. No. 10/737,705, the disclosures of which are incorporated herein by reference. The prostheses and methods described therein help establish a desired anatomy to a spine and return a desired range of mobility to an individual. Such prostheses and methods also help lessen or alleviate spinal pain by relieving the source of nerve compression or impingement.

SUMMARY OF THE INVENTION

What is needed are methods and tools for facilitating the sizing, orientation and implant of spine prostheses such as artificial facet joint prostheses. The present invention provides tools and methods designed to aid in the placement of facet joint prostheses at virtually all spinal levels including, but not limited to, L1–L2, L2–L3, L3–L4, L4–L5, L5–S1, T11–T12, and T12–L1.

For the sake of description herein, the tools and prostheses that embody features of the invention are identified as either "cephalad" or "caudal" with relation to the portion of a given natural facet joint they replace. As previously described, a natural facet joint, such as facet joint 32 (FIG. 3), has a superior half and an inferior half. In anatomical terms, the superior half of the joint is formed by the vertebral level below the joint, which can thus be called the "caudal" portion of the facet joint because it is closer to the feet of the person. The inferior half of the facet joint is formed by the vertebral level above the joint, which can thus be called the "cephalad" portion of the facet joint because it is closer to the head of the person. Thus, the prosthesis and tool that are used in the replacement of the caudal portion of a natural facet joint (i.e., the superior half) will be called a "caudal" prosthesis. Likewise, the prosthesis and tool that are used in the replacement of the cephalad portion of a natural facet joint (i.e., the inferior half) will be called a "cephalad" prosthesis.

Because the specific features of a patient's spinal anatomy can vary significantly from patient to patient (and can also vary within the various spinal levels of an individual patient or even vary between the facet joints in a single vertebral level), a prosthesis suitable for implantation into a patient will desirably be configured or tailored to accommodate the specific features of the patient's spinal anatomy. For example, the size, spacing and orientation of the pedicles, lamina and associated spinal anatomy, as well as the size, spacing and orientation of the individual facet joints to be replaced, can vary widely depending upon the level and/or patient to be treated.

In order to accommodate such variations in anatomy, a configurable and/or modular prosthesis system (comprising multiple configurable and/or interchangeable components of varying shapes and/or sizes) may be used to tailor the prosthesis to the varying anatomical demands of a given patient. Once the surgical site has been prepared, the prosthesis can be assembled and/or configured from components chosen by the physician based on anatomical measurements of the treatment site during the surgery. The disclosed invention desirably facilitates such measurements of the treated anatomy.

In one aspect, the present invention provides a measurement tool for configuring and installing a cephalad facet joint prosthesis including a fixation measurement element and a support arm element. This measurement tool assists in the selection of a cephalad facet joint prosthesis for implantation in a patient. The measurement tool can be used in the determination of the dimensions of a cephalad facet joint prosthesis. Particularly, this measurement tool can be used to determine the length of the fixation element and support arm element of the cephalad facet joint prosthesis.

In some embodiments, the connection between the fixation measurement element and support arm element is a polyaxially adjustable connection. In one embodiment, the fixation measurement element has indentations which control the vertical movement of the support arm element. The indentations on the fixation measurement element can also permit the determination of the length of the fixation element of a cephalad facet joint prosthesis.

In one embodiment, the support arm element supports a trial facet joint bearing surface. The bearing surface is intended to predict the location of the facet joint bearing surface of an actual prosthesis intended for implantation in a patient.

The fixation measurement element in one embodiment is adapted and configured to permit measurements for determination of the length of the fixation element of a cephalad facet joint prosthesis for implantation in a patient. In another embodiment, the fixation measurement element includes markings to assist in the determination of the length of the fixation element of a cephalad facet joint prosthesis.

In another aspect, the present invention provides a caudal facet joint prosthesis measurement system including a stem element and a trial caudal bearing surface element connected to each other by a fastener or fastening mechanism. This measurement tool assists in the selection of a caudal facet joint prosthesis for implantation in a patient. The measurement tool can be used in the determination of the dimensions of a caudal facet joint prosthesis. Particularly, this measurement tool can be used to determine the length of the fixation element of the caudal facet joint prosthesis to be implanted in a patient. Also, this tool can be used to determine the angle between the artificial facet joint element and fixation element of the caudal facet joint prosthesis. If desired, the mechanism can permit motion between the elements for alignment purposes and also allow locking of the chosen configuration/orientation once determined.

In one embodiment, the fastener used in the caudal facet joint prosthesis measurement tool is a screw. Examples of other suitable fasteners could include stems, posts, threads, polyaxial mechanisms, splines, tapers, press fits, bayonet, cap screws, ball detents, friction fits, cams, collets and/or clamps. In certain embodiments, the fastener permits vertical movement of the trial caudal bearing surface element along the stem element. In other embodiments, the fastener permits rotation of the trial caudal bearing surface element in different planes with respect to the stem element. These planes can include movement along the axial and median planes.

In another embodiment, the stem element is adapted and configured to permit measurement of the length of a fixation element of a caudal facet joint prosthesis to be implanted in a patient. In yet another embodiment, the stem element of the measurement tool includes markings to permit the measurement of the length of the fixation element.

In one of the embodiments, the measurement tool for the caudal facet joint prosthesis is adapted and configured to permit measurement of the angle between the artificial facet joint element and fixation element of a caudal facet joint prosthesis to be implanted in a patient. The angle measurements can include measurements in the median, horizontal and frontal planes (such measurements could also include measurements relative to the coronal, sagittal and/or axial planes, if desired). In one embodiment, to facilitate the determination of the angle measurement, the trial caudal bearing surface element is adapted and configured to interact with a measurement tool holder.

In one aspect, the invention is a measurement tool holder including a measurement surface connected to a holder element. This tool holder assists in determining the angle measurements obtained with the caudal facet joint prosthesis measurement tool. The caudal facet joint prosthesis measurement tool can be placed in the tool holder and the angle between the artificial facet joint element and fixation element of a caudal facet joint prosthesis can be determined.

In one embodiment, the measurement tool holder is adapted and configured to hold the measurement tool for the caudal facet joint prosthesis. In yet another embodiment, the measurement surface of the tool holder includes two plates at right angles to each other. The plates can include markings to permit determination of the angle measurements, preferably in the horizontal and median planes.

Another aspect of the invention provides a method for determining the dimensions of a cephalad facet joint prosthesis to be implanted in a patient. The method includes the steps of forming a hole at a location in the vertebra and placing a fixation measurement element of a cephalad facet joint prosthesis measurement tool into the hole. Further optional steps include the steps of obtaining a first length measurement to determine length of a fixation element of a cephalad facet joint prosthesis to be implanted in a patient; and obtaining a second length measurement for determining the length of a support arm element of the cephalad facet joint prosthesis. In various embodiment, the measurement tool can be used in conjunction with a caudal prosthesis or other implanted device, or can be used in conjunction with the caudal joint surface or other natural anatomical landmark.

Yet another aspect of the invention provides a method for determining the dimensions of a caudal facet joint prosthesis to be implanted in a patient. The method includes the steps of forming a hole at a location in the vertebra and placing a caudal facet joint prosthesis measurement tool into the hole. Further optional steps include the steps of obtaining a length measurement which indicates the length of a fixation element of a caudal facet joint prosthesis to be implanted in a patient; and obtaining an angle measurement which indicates the angle between a artificial facet joint element and a fixation element of the caudal facet joint prosthesis. In an alternate embodiment, the external surfaces of the measurement tool could incorporate calibrated markings allowing angle measurements to be determined without an associated measurement fixture.

BRIEF DESCRIPTION OF THE DRAWINGS

FIG. 7 is a perspective view of one embodiment of a caudal prosthesis for replacing the superior half of a natural facet joint on an inferior vertebral body;

DETAILED DESCRIPTION OF THE PREFERRED EMBODIMENT

Although the disclosure presented herein provides details to enable those skilled in the art to practice various embodiments of the invention, the physical embodiments disclosed herein merely exemplify the invention which may be embodied in other specific structures. Accordingly, while preferred embodiments of the invention are described below, details of the preferred embodiments may be altered without departing from the invention. All embodiments that fall within the meaning and scope of the appended claims, and equivalents thereto, are intended to be embraced by the claims.

Figure 5A:
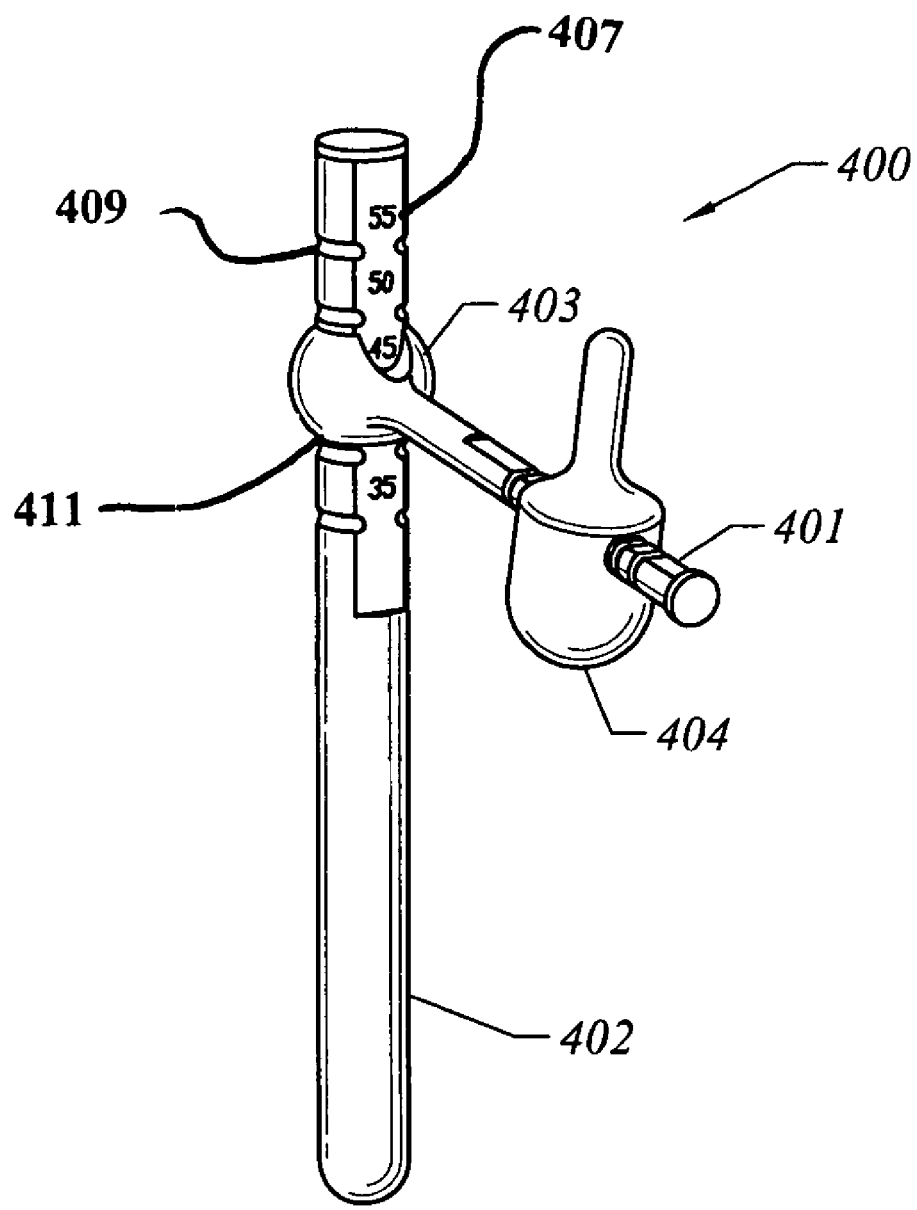
FIGS. 5A and 5B are views of one embodiment of a measurement tool for installing a cephalad facet joint prosthesis.
Figure 5B:
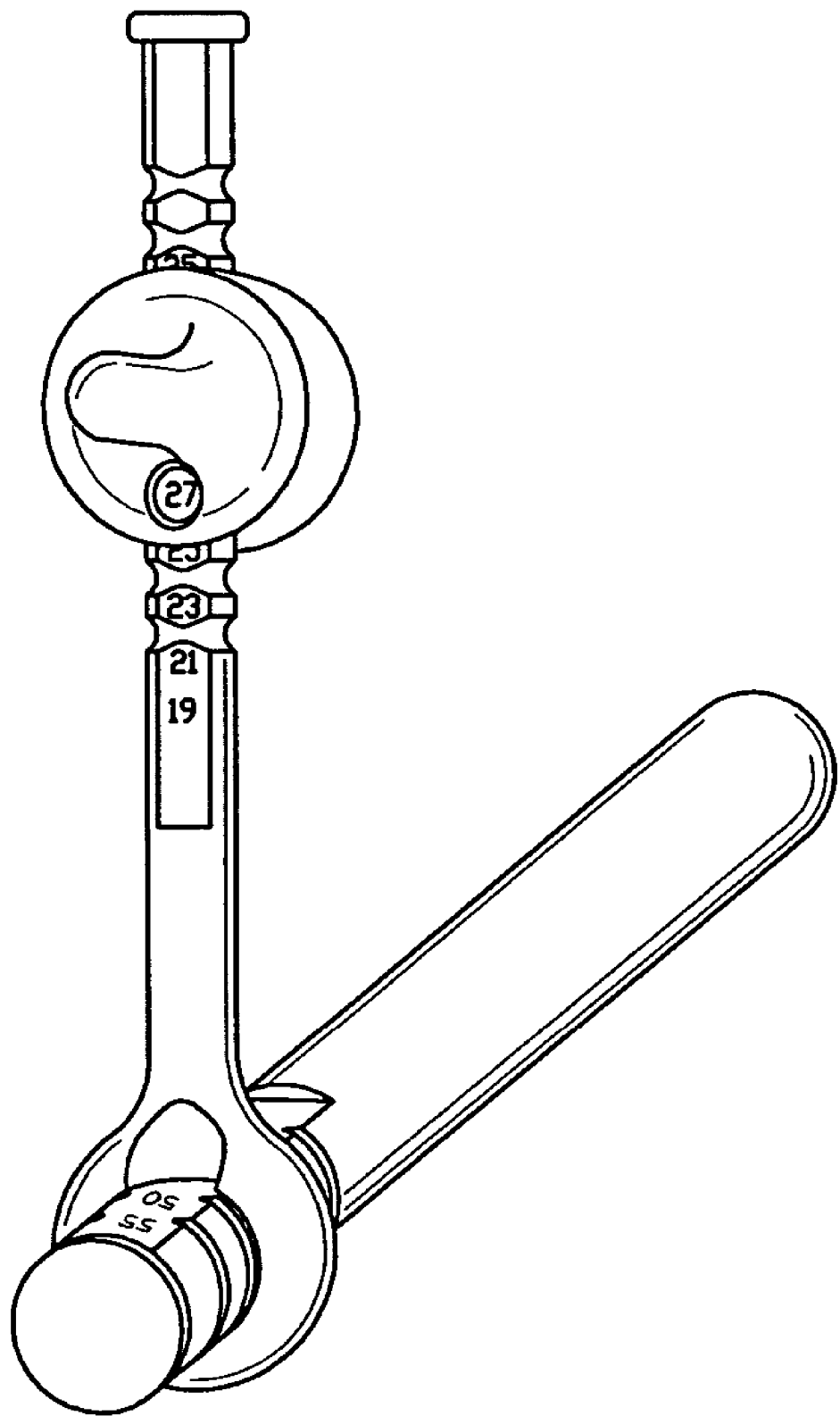
Figure 6A:
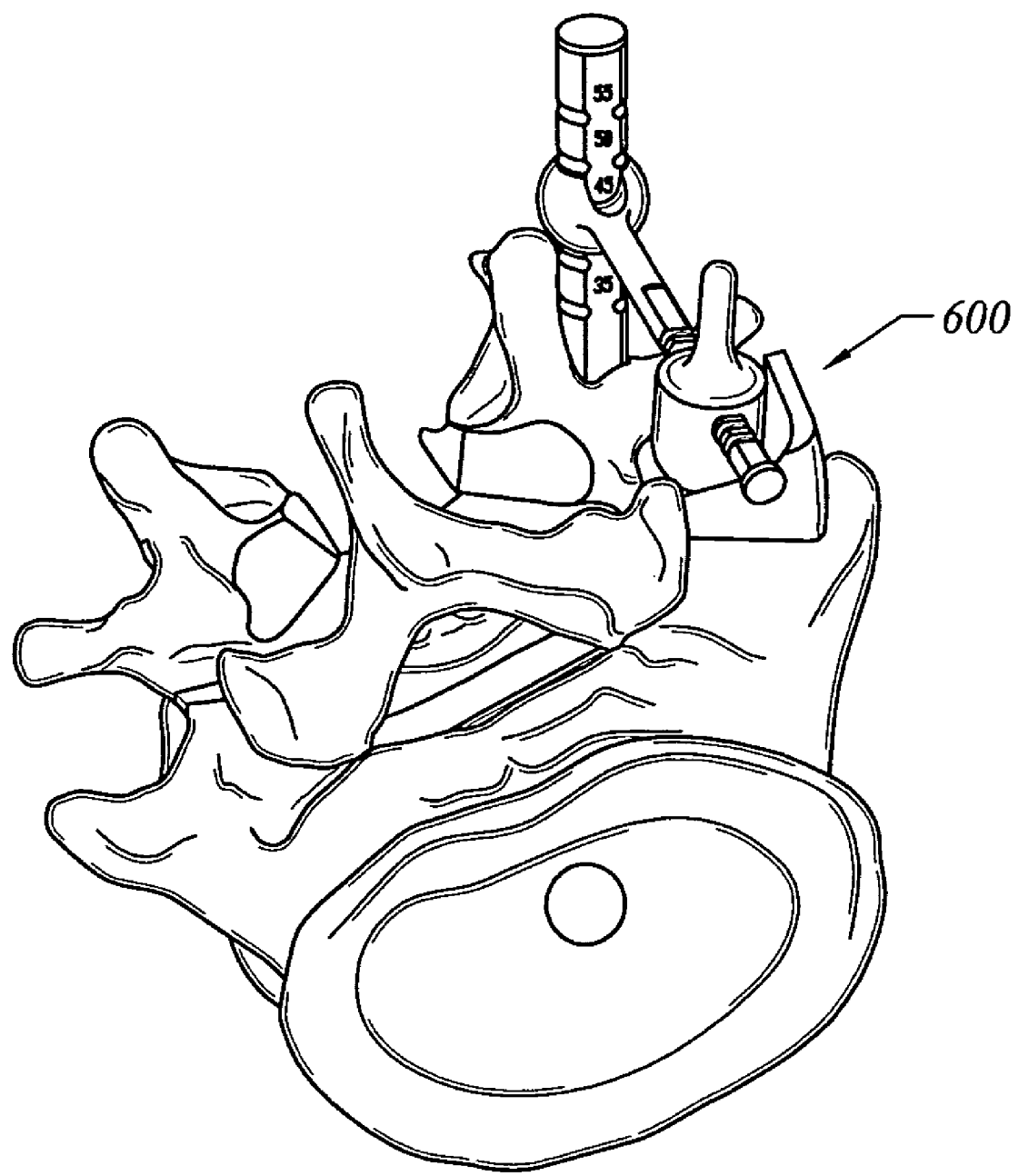
FIGS. 6A, 6B and 6C are views of one embodiment of an installed measurement tool for a cephalad facet joint prosthesis.
Figure 6B:
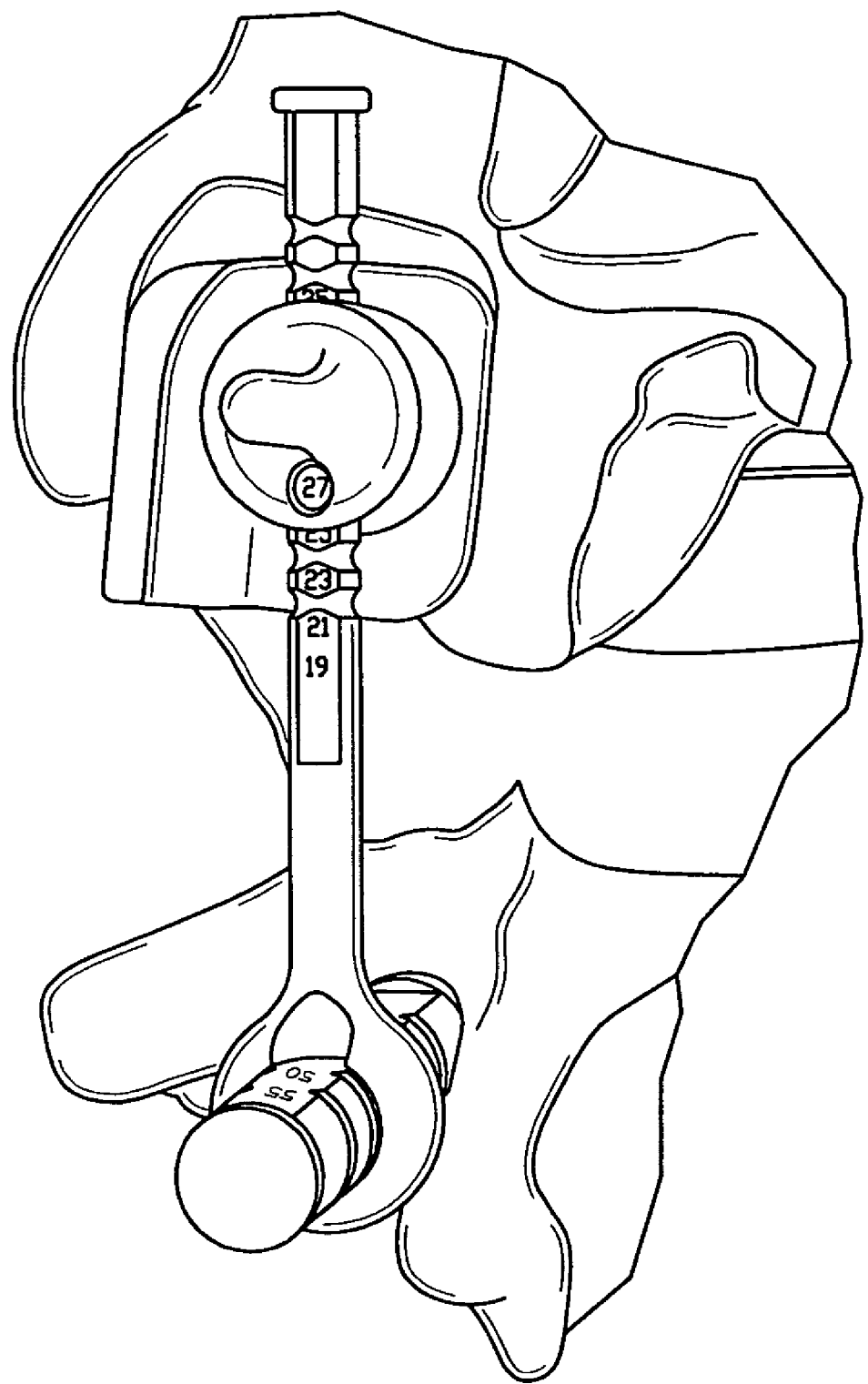
Figure 6C:
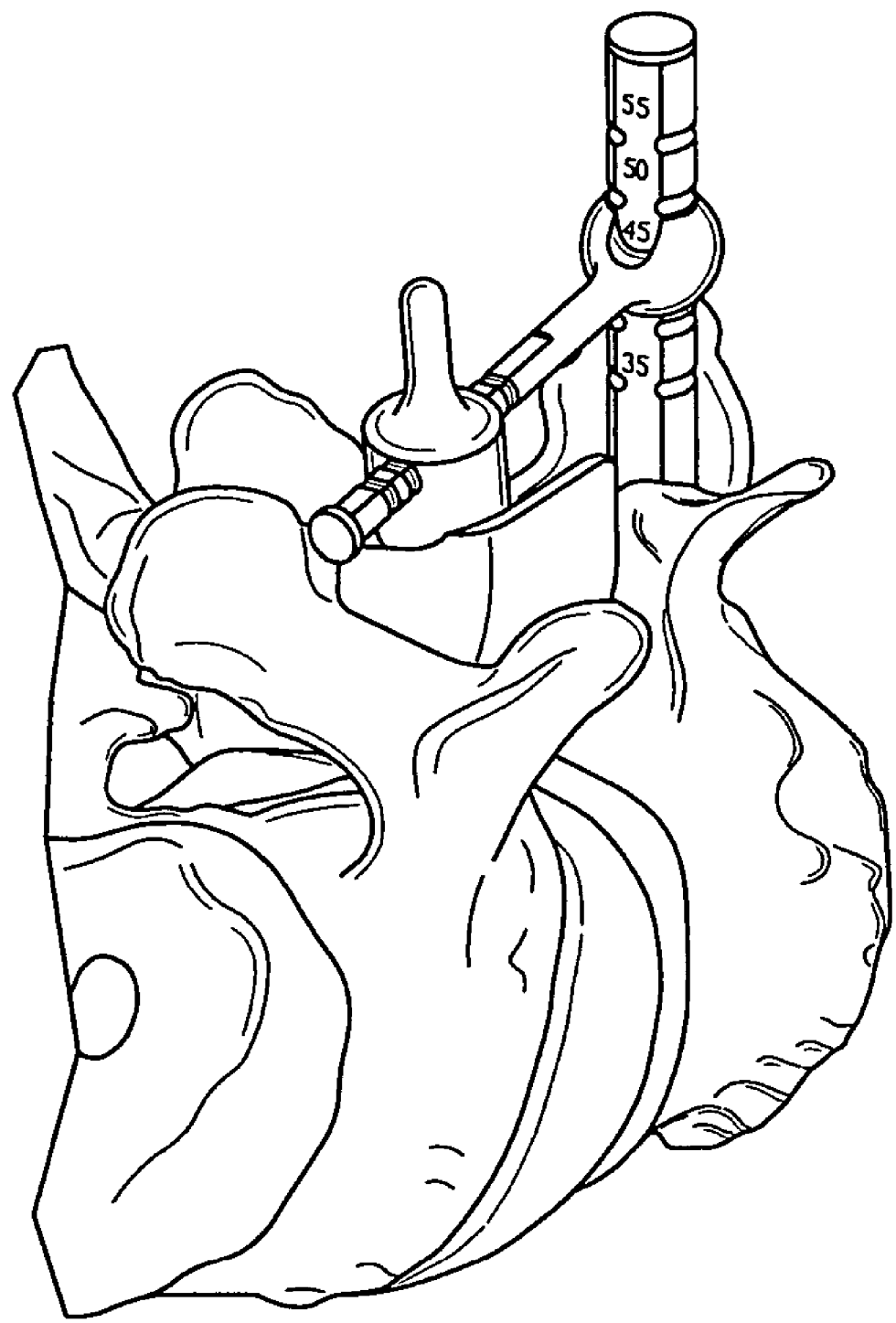

FIGS. 5 and 6 depict one embodiment of a measurement tool for installing a cephalad facet joint prosthesis. The measurement tool can be used to assist in the installation of cephalad facet joint prostheses such as those described in U.S. patent application Ser. No. 10/737,705 or other cephalad facet joint prostheses.

Figure 1:
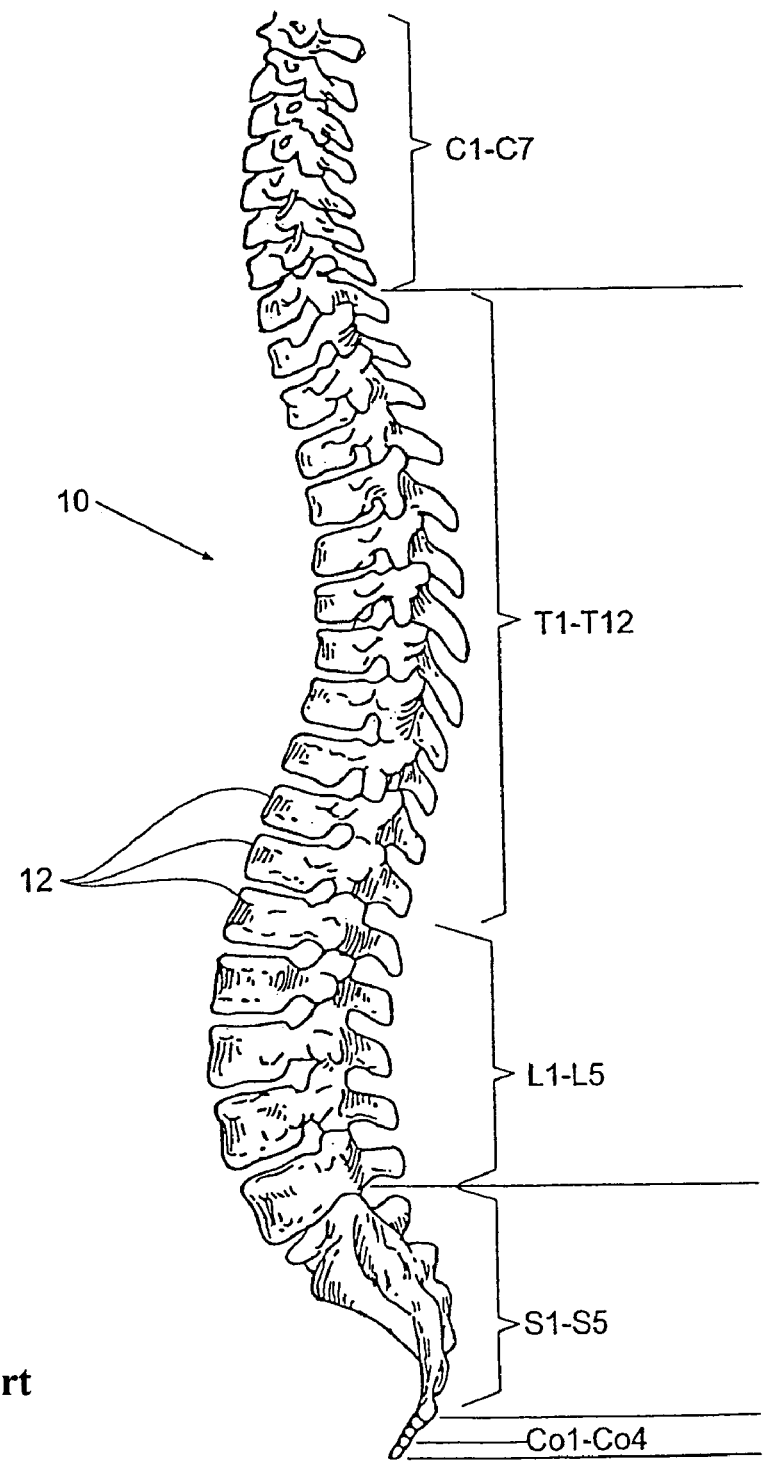
FIG. 1 is a lateral elevation view of a normal human spinal column.
Figure 2:
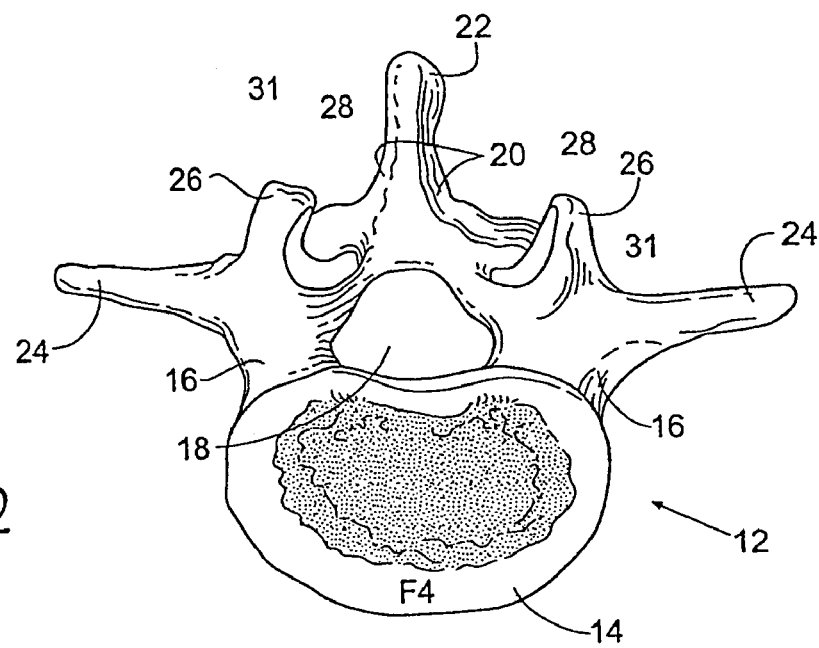
FIG. 2 is a superior plan view of a normal human lumbar vertebra.
Figure 3:
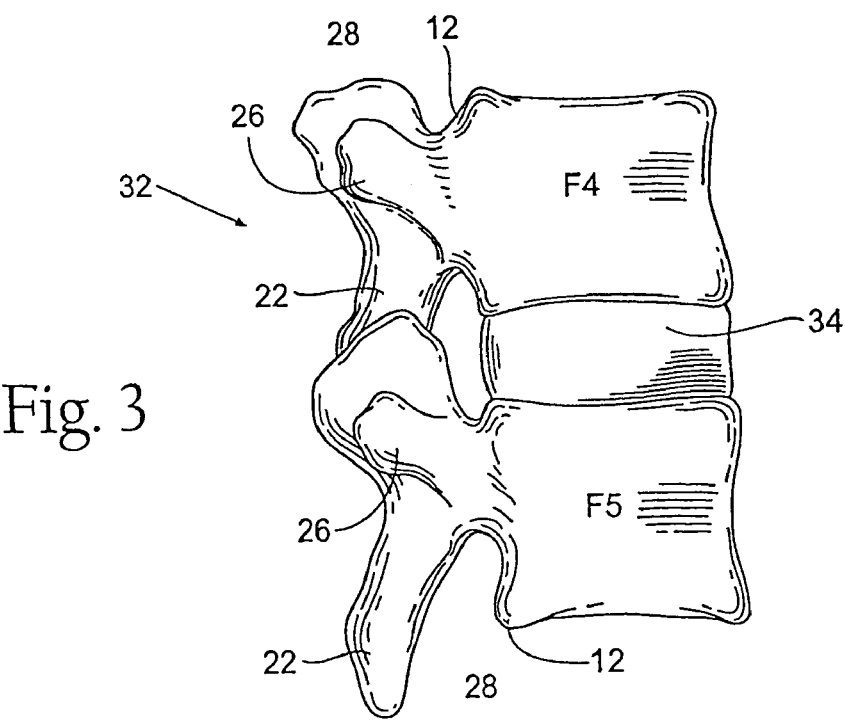
FIG. 3 is a lateral elevation view of adjoining normal human lumbar vertebrae L4 and L5.
Figure 4:
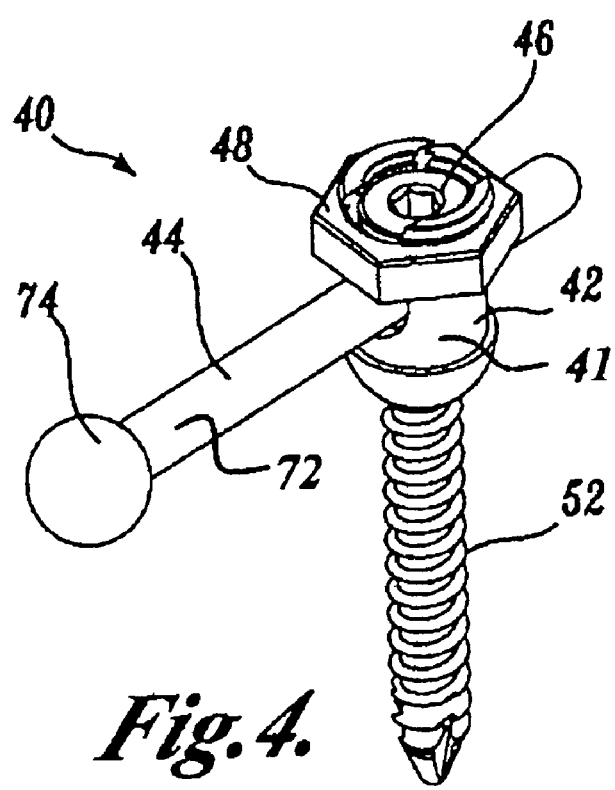
FIG. 4 is a perspective view of one embodiment of a cephalad facet joint prosthesis for replacing the inferior half of a natural facet joint on a superior vertebral body.

For purposes of illustrating the invention, one example of a cephalad facet joint prosthesis that is suitable for use with the measurement tools and methods described herein is depicted in FIG. 4. FIG. 4 shows an artificial cephalad facet joint prosthesis 40 configured to replace the inferior articulating process of a facet joint, such as after the surgical removal of the articulating process. When the cephalad prosthesis 40 is attached to a vertebra, the artificial facet joint element 44 articulates with the superior half of the facet joint 32. In this example, prosthesis 40 includes an artificial facet joint element 44 connected to a fixation element 52 via a polyaxial connection 41 that permits facet joint element 44 and fixation element 52 to be rotated with respect to each other around more than one axis. A fixing nut 48 is threadably engaged with the outer periphery of base 42 above the artificial facet joint element 44. Similarly, a set screw 46 is threadably engaged with the inner periphery of base 42 above the artificial facet joint element 44. The artificial facet joint element 44 includes a support arm 72 and a facet joint bearing surface 74.

As shown in FIGS. 5A and 5B, a measurement tool 400 suitable for use in installing and configuring the prosthesis of FIG. 4 includes a support arm element 401 and a fixation measurement element 402 via a polyaxial connection element 403. The polyaxial connection element 403 permits movement of the support arm element 401 along the fixation measurement element 402 in multiple axes. The connection 403 permits vertical movement of the support arm element 401 along the fixation measurement element 402 (or fixation element) and also permits horizontal movement of the support arm element 401 relative to the fixation measurement element 402. In this manner, the measurement tool contains aspects of the actual prosthesis. Measurement tools optimized to aid in the implantation of other spine prostheses may have other features containing aspects of those prostheses.

The fixation measurement element 402 is adapted and configured to permit measurement of the length of a fixation element of a cephalad facet joint prosthesis to be installed in a patient. Preferably, markings 407 are present on the fixation measurement element 402 which permit the determination of this length measurement. Typically, a hole is formed in the vertebra of the patient at a location wherein the cephalad facet prosthesis is intended to be installed and the measurement tool 400 is placed in this hole. The tool 400 is adjusted to a position similar to that of the cephalad facet joint prosthesis, and then the penetration depth of the fixation measurement element 402 into the hole is determined. This penetration depth assists the user in choosing the length of the fixation element required to attach the cephalad facet joint prosthesis to the vertebra.

In one embodiment, the fixation measurement element 402 includes indentations such as those depicted in FIG. 5A. The indentations 409 provide stops for the vertical movement of the support arm 401 along the fixation measurement element 402, e.g. by engaging a ridge 411 in a support arm 401. The indentations 409 can also permit the determination of the length of the fixation element 52 of a cephalad facet joint prosthesis 40 to be installed in a patient. The indentations 409 may be formed at intervals corresponding to various fixation stems or screw lengths contained in a modular component kit.

Similarly, another length measurement can be obtained using the support arm element 401. Once the measurement tool 400 is placed into the hole drilled in the vertebra, the support arm is positioned into a location wherein the artificial facet joint element 44 of the cephalad facet joint prosthesis 40 would be located. The distance between the fixation measurement element 402 and the putative location of facet joint bearing surface 74 of the cephalad facet joint prosthesis 40 is measured along the support arm element 401. This measurement is used to select the length of the support arm 72 of the cephalad facet joint prosthesis 40 to be implanted in a patient. Alternatively, the measurement could correspond to a color coding or number/letter designation that is used to determine the appropriate correspondingly-identified prosthesis.

In one embodiment, a trial facet joint bearing surface 404 can be attached to the support, arm element 401. The trial facet joint bearing surface 404 may be placed in the location that the actual cephalad facet joint prosthesis 40 would be placed and then the length measurement can be obtained which can be used to select the length of the support arm 72 of the cephalad facet joint prosthesis 40. Once again, the relationship between the measurement tool's fixation measurement element, support arm element and trial facet joint bearing surface corresponds to aspects of the actual facet joint prosthesis whose implant the tool is assisting. Other measurement tools and methods having aspects corresponding to other spine implant features are within the scope of this invention.

Another aspect of the invention is a method of using the measurement tool 400 to measure the dimensions of a cephalad facet joint prosthesis 40 to be used in total facet joint replacement. The cephalad prosthesis 40 is typically attached to a vertebra to replace the articulating function of the cephalad portion of the natural facet joint. FIG. 6 shows different views of a measurement tool 400 placed into a vertebra. In one embodiment, for obtaining the measurements, the cephalad measurement tool 400 can be placed in one vertebra and a caudal facet joint prosthesis 600 can be placed in the inferior adjoining vertebra, as depicted in FIG. 6. The caudal facet joint prosthesis can be a trial prosthesis or the actual prosthesis. When the measurement tool 400 is used with a caudal facet joint prosthesis, it is preferred that the support arm element 401 bear a trial facet joint bearing surface 404. To obtain the length measurements, a hole is formed in the location where the actual cephalad prosthesis 40 is to be placed and into this hole the measurement tool 400 is placed. The tool is placed in the hole at a depth that is similar to the depth at which actual cephalad prosthesis 40 is to be placed. The support arm 401 is moved horizontally and/or vertically with respect to the fixation measurement element 402 and placed at about the same location that the artificial facet joint element 44 would be placed. If the measurement tool 400 includes a trial cephalad facet joint bearing surface 404 and is used in combination with a caudal facet joint prosthesis, the trial facet joint bearing surface 404 is placed in the bearing surface of the caudal prosthesis prior to taking the measurements. In one embodiment, as shown in FIGS. 5B and 6B, to determine the length of the support arm 72 of the actual cephalad prosthesis, a window on the trial facet joint bearing surface 404 can be used to read the length from the support arm element 401. As mentioned above, the length of the fixation element 52 can be determined from the fixation measurement element 402. Markings and/or indentations on the fixation measurement element 402 can be used to determine the required length of the fixation element 52.

FIGS. 8–10 depict one embodiment of a measurement tool for installing a caudal facet joint prosthesis. The measurement tool can be used to assist in the installation of caudal joint prostheses such as those described in U.S. patent application Ser. No. 10/737,705 or other caudal facet joint prostheses.

One embodiment of a caudal facet joint prosthesis that is suitable for use with the measurement tool described herein is depicted in FIG. 7. FIG. 7 shows an artificial caudal facet joint prosthesis 100 configured to replace the superior portion of a natural facet joint, such as after the surgical removal of the articulating process forming the superior portion of the facet joint. Prosthesis 100 includes an artificial facet joint element 104 connected to a fixation element 116 via a polyaxial connection 115 that permits facet joint element 104 and fixation element 116 to be rotated with respect to each other around more than one axis. The polyaxial connection 115 of caudal prosthesis 100 includes a base 112 connected to a support arm 102 of facet joint element 104. The artificial facet joint element 104 includes a bearing surface 118. A fixing nut 108 is threadably engaged with the outer periphery of base 112 above the artificial facet joint element 104. Similarly, a set screw 106 is threadably engaged with the inner periphery of base 112 above the artificial facet joint element 104.

Figure 8A:
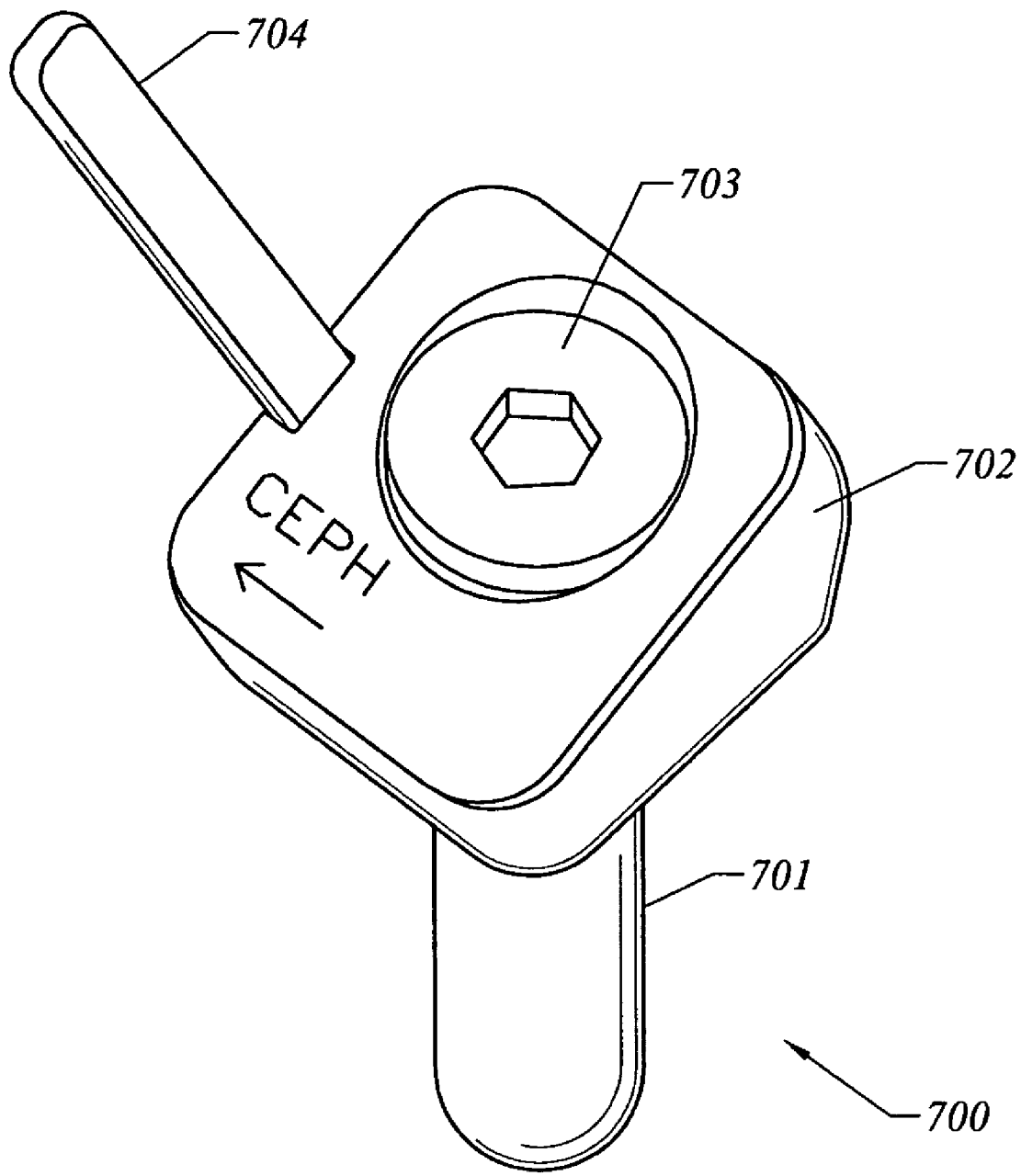
FIGS. 8A and 8B are views of one embodiment of a measurement tool for installing a caudal facet joint prosthesis.
Figure 8B:
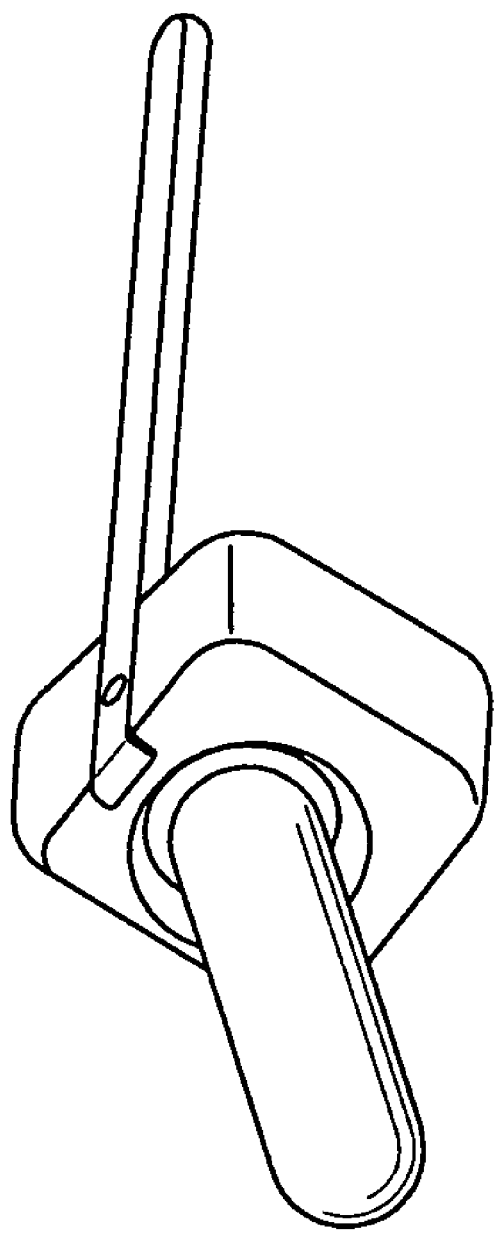
Figure 9A:
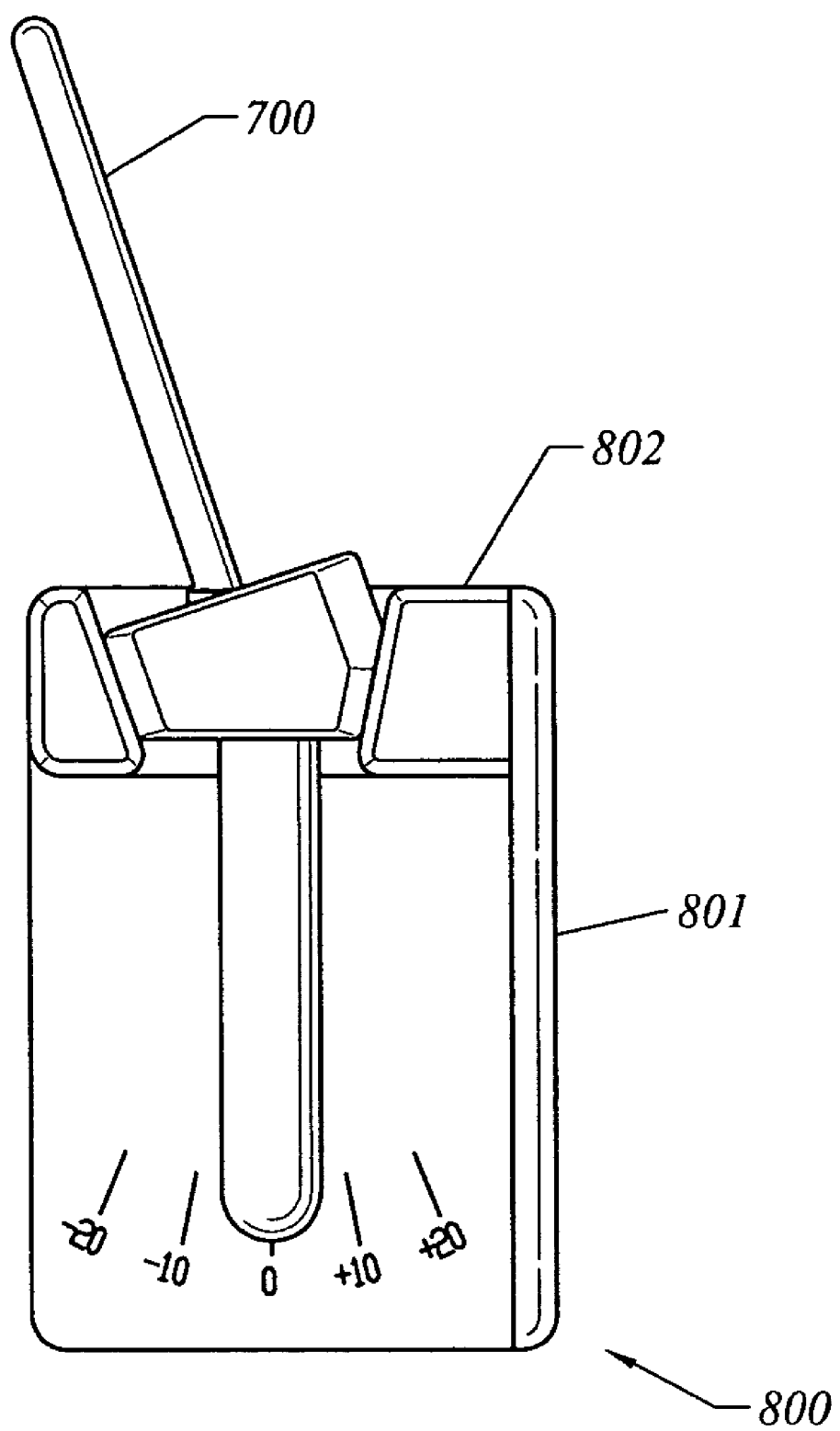
FIGS. 9A–D are views of one embodiment of a measurement tool holder for holding a measurement tool for a caudal facet joint prosthesis.
Figure 9B:
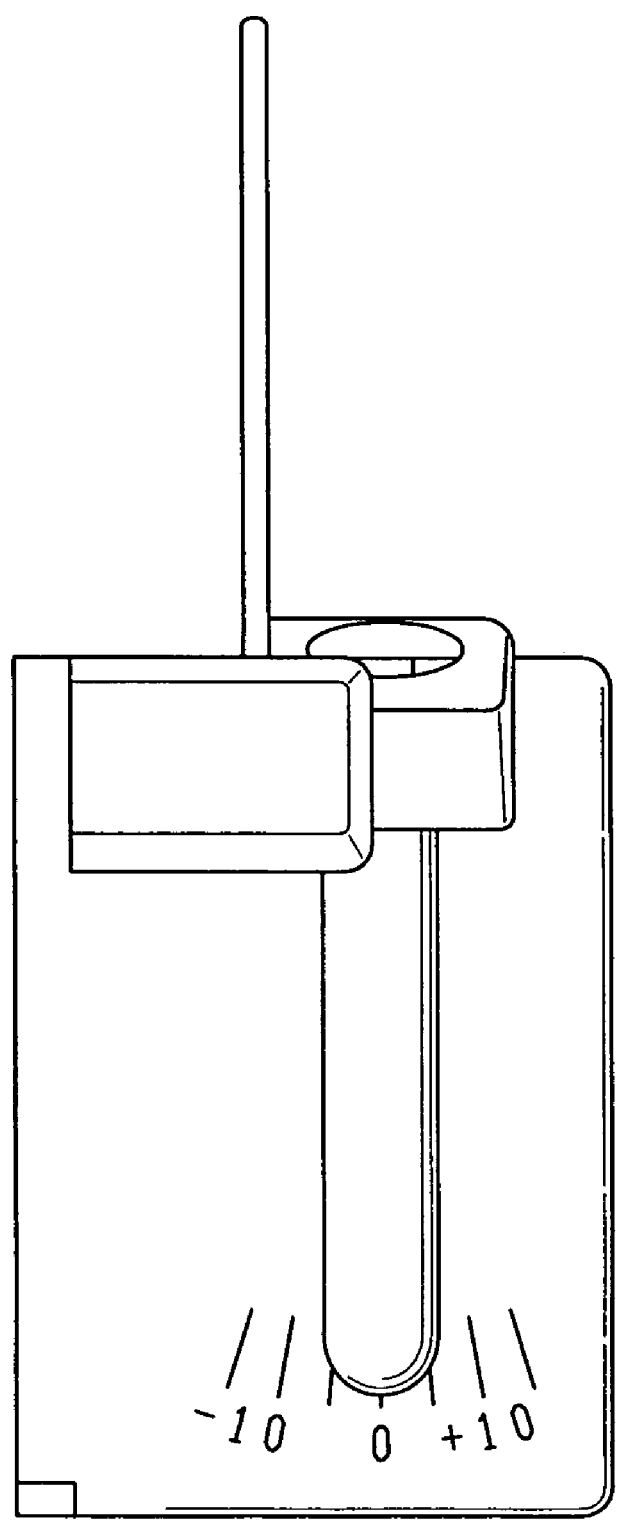
Figure 9D:
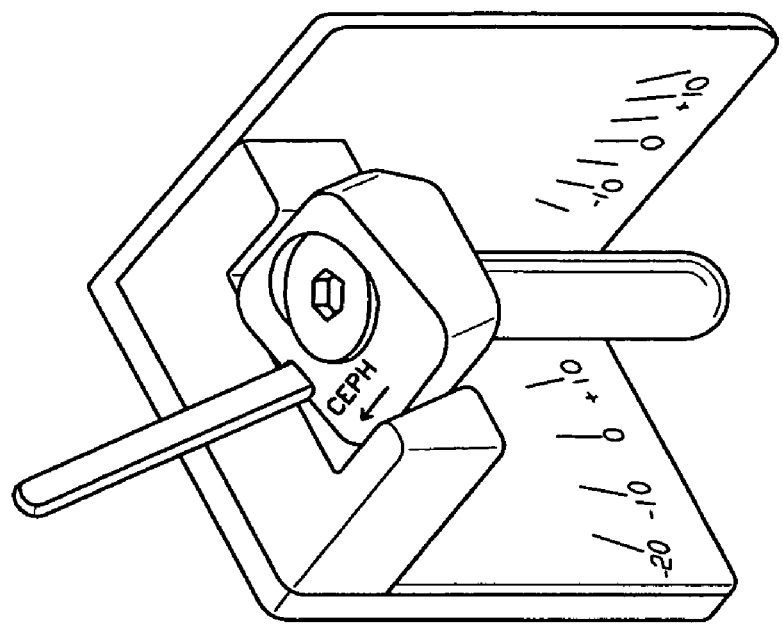
Figure 9C:
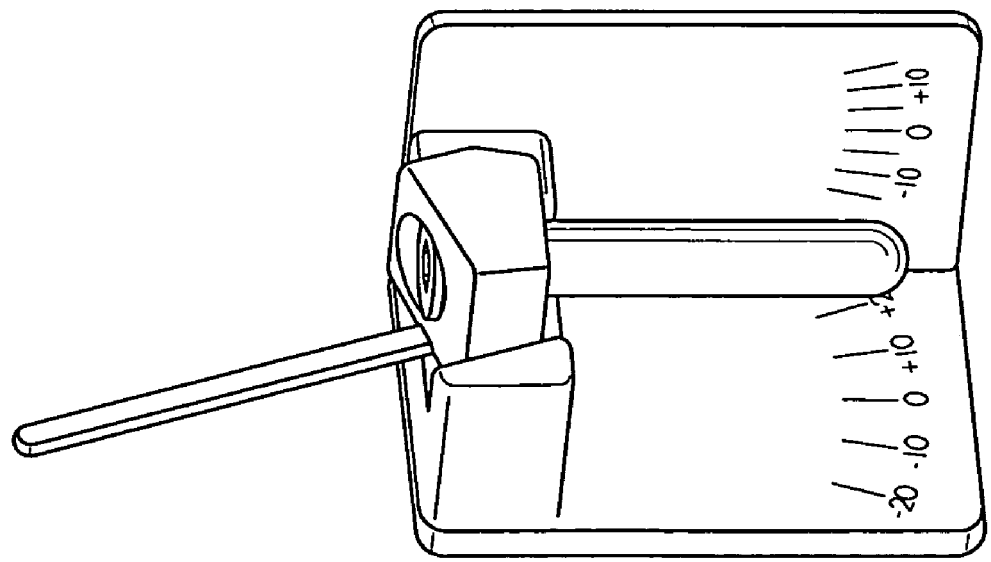

A measurement tool 700 suitable for use with the caudal facet joint prosthesis shown in FIG. 7 is shown in FIGS. 8A and 8B. Measurement tool 700 includes a stem element 701 connected to a trial caudal bearing surface 702 via a fastener 703. Thus, measurement tool 700 contains aspects of the caudal facet joint prosthesis whose implant the tool is assisting. In the embodiment depicted in FIG. 8A, the fastener 703 is a set screw. In other embodiments other suitable fasteners can be employed, including, but not limited to, stems, posts, threads, polyaxial mechanisms, splines, cap screws, ball detents, friction fits, tapers, press fits, bayonet, cams, collets and/or clamps.

The stem element 701 is adapted and configured to obtain length measurements which would correspond to the length of the fixation element 116 of the caudal facet joint prosthesis 100. The stem element can include markings and/or indentations to assist in obtaining the measurements. If desired, multiples stem elements of varying diameters can be utilized in a similar fashion to size and/or determine the diameter and dimensions of the hole.

The trial caudal bearing surface 702 helps determine the relative positions of, and the angle between, the prosthesis's fixation element and its bearing surface. The trial caudal bearing surface 702 is capable of movement along multiple planes and can rotate relative to the stem element 701 via a lockable ball-joint. If desired, an alternate embodiment of the bearing surface 702 can move vertically (not shown) along the stem element 701, to permit sizing of the stem element. Other planes of movement can include the median, horizontal and frontal planes. In another embodiment, the caudal bearing surface 702 is connected to a handle 704. The handle 704 allows the user to move the caudal bearing surface 702 into the desired location and also position it in the right plane. Typically, the handle 704 permits movement of the caudal bearing surface 702 in various planes for alignment. Also, the handle 704 can permit the user to place the stem 701 of the tool into the hole drilled in the vertebra.

In one alternate embodiment, the handle 704 can comprise a radiopaque material with the handle 704 used for fluoroscopic alignment of the caudal bearing surface 702. In this embodiment, the handle 704 and upper end plate of the caudal vertebral body (not shown) can be examined in a medial-lateral image (using non-invasive and/or fluoroscopic imagine apparatus) of the surgical area. A comparison of the orientation of the handle 704 and the orientation of the upper end plate can be made to determine the desired alignment and positioning of the caudal bearing surface. In one embodiment, the orientation of the handle and the upper end plate can be parallel or nearly parallel.

Another aspect of the invention is a measurement tool holder for use with the caudal measurement tool described above or another measurement tool. One embodiment of the measurement tool holder is depicted in FIGS. 9A–D. In this embodiment, the measurement tool holder 800 includes a measurement surface 801 and a holder element 802. In one embodiment, the measurement surface 801 includes two plates attached to each other at a right angle. The measurement surface 801 is adapted and configured to measure the angle between the caudal bearing surface 702 and stem 701. This angle measurement is typically used by a user to select, assembly and/or configure a caudal prosthesis for implantation into a patient, such as caudal prosthesis 100 of FIG. 7. For example, the selected caudal prosthesis may have an angle measurement between its bearing surface 118 and its fixation element 116 similar to the angle measurement obtained from the caudal measurement tool 700 and measurement tool holder 800. Alternatively, the prosthesis may be configurable to orient its fixation element and its bearing surface to match the measured angle.

In one embodiment, the tool holder's measurement surface 801 includes markings to assist in obtaining the desired angle measurements. Also, the top surface of the measurement surface 801 may have a holder element 802 attached thereto. The holder element 802 can be, for example, a square or rectangular block with a portion of the block cut out to fit the caudal bearing surface 702 of the caudal measurement tool 700. The portion of the holder element 802 that holds the caudal bearing surface 702 is cut out in a shape that is suitable for holding the caudal bearing surface 702. Thus, the shape of the cut out portion of the holder element 802 will vary depending on the shape of the caudal bearing surface 702 to be used with the measurement holder 800.

Figure 10A:
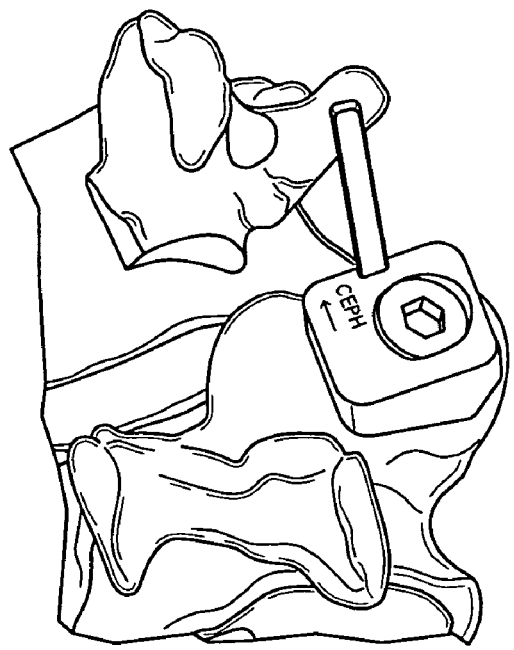
FIGS. 10A and 10B are views of one embodiment of an installed measurement tool for a caudal facet joint prosthesis.
Figure 10B:
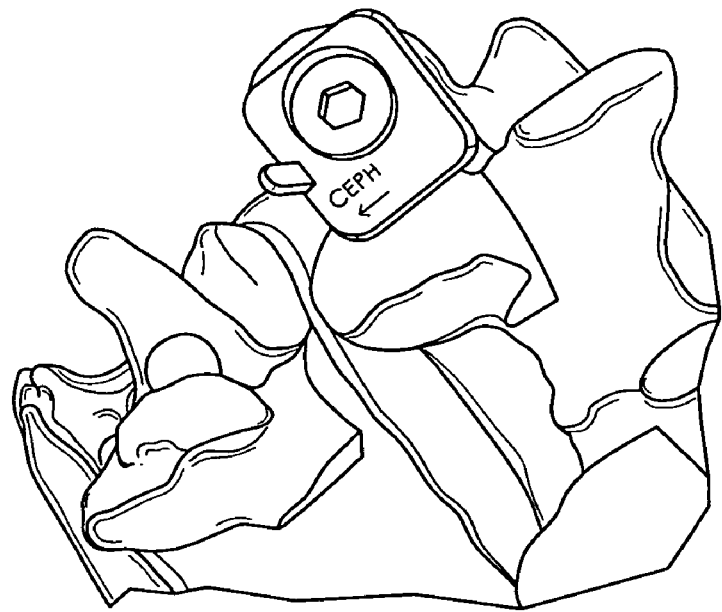

One aspect of the invention is a method for using the caudal measurement tool 700 in combination with, for example, the measurement tool holder 800 described above or with the cephalad measurement tool 400 described above. In one embodiment, a hole is formed at a suitable location in the vertebra (such as by drilling) wherein a caudal prosthesis 100 is intended to be placed. This location typically is the best location for the placement of the caudal prosthesis based on the condition of the bone, easy access to the location, etc. Into this hole the caudal measurement tool 700 is placed in a manner as shown in FIGS. 10A and 10B.

The caudal measurement tool 700 may be placed into the hole using the handle 704. The handle 704 and the set screw 703 are used to place the measurement tool at the required depth and also to place the caudal bearing surface 702 at the required angle. To obtain the appropriate angle of the caudal bearing surface 702 with respect to the stem 701, the fastener 703 is loosened and the caudal bearing surface 702 is positioned at the appropriate angle. Once the appropriate angle is obtained (typically based on orientation relationships with anatomical landmarks, which can include the orientation of the cephalad bearing surface as well as anatomical positioning and/or intervening anatomical features), the fastener 703 is tightened to maintain the angle for measurement purposes. In one embodiment, the caudal measurement tool 700 is used in combination with a cephalad prosthesis (such as cephalad prosthesis 40 described above) or a cephalad measurement tool (such as tool 400 described above). When used in combination with a cephalad prosthesis or a cephalad measurement tool, the caudal bearing surface 702 is placed in contact with the facet joint bearing surface of the cephalad prosthesis or the trial facet joint bearing surface. Then, the position of the caudal bearing surface 702 is adjusted by manipulating the fastener 703 (as described above) to get good articulation with the facet joint bearing surface or the trial facet joint bearing surface.

After the caudal measurement tool 700 is appropriately placed, the length and angle measurements are obtained. Preferably, the caudal measurement tool 700 is removed from the hole to take the measurements. One of the measurements that can be obtained with the caudal measurement tool 700 is the fixation length measurement. This measurement is obtained from the stem element 701 and indicates the length of the fixation element 116 of the caudal prosthesis to be implanted in a patient. Also, the caudal measurement tool 700 can be used to obtain an angle measurement between the caudal bearing surface 702 (or alignment fixation measurement) and stem element 701. This measurement may be obtained by placing the caudal measurement tool 700 into a measurement tool holder (such as holder 800 described above) and reading the angle, such as from a measuring surface 801. When used with the caudal prosthesis 100 of FIG. 7, this angle measurement is used to determine the angle between the artificial facet joint element 104 and fixation element 116 of the caudal prosthesis 100. In one alternate embodiment, the caudal bearing surface is positioned and secured to the vertebral body first, and then the cephalad bearing surface is positioned and secured relative to the caudal bearing surface.

One aspect of the invention is a method for selecting suitable caudal and/or cephalad prostheses from a set of prostheses for implantation into a patient. In one embodiment, the cephalad measurement tool 400 is used to obtain the two length measurements from the fixation measurement 402 and support arm 401. A user uses these measurements to select a suitable cephalad prosthesis 40 for implantation in a patient. The selected prosthesis preferably has a fixation element 52 length and support arm 72 length that are similar to the support arm 401 and fixation measurement 402 length measurements, respectively, obtained from the cephalad measurement tool 400. The term "similar" is used to herein to mean values that correspond to each other but are not necessarily identical. In another embodiment, the caudal measurement tool 700 is used to obtain length and angle measurements and a user uses these measurements to select a suitable cephalad prosthesis for implantation in a patient. The selected prosthesis preferably has a stem 701 length similar to the length measurement from the caudal tool 700 and has an angle between the artificial facet joint element and fixation element similar to the angle measurement obtained from the tool.

While preferred embodiments of the invention have been illustrated and described, it will be appreciated that various changes can be made therein without departing from the spirit and scope of the invention. Moreover, while the present inventions have been described for use with a modular prosthesis system, it should be understood that the present inventions have utility in conjunction with the measurement and placement of other prosthesis systems, including single component, multi-component and custom-made prosthesis, with varying results. Further, the trialing system described herein can comprise single or multi-component tools and devices.

All publications and patent applications mentioned in this specification are herein incorporated by reference to the same extent as if each individual publication or patent application was specifically and individually indicated to be incorporated by reference.

What is claimed is:

1. A caudal facet joint prosthesis measurement system comprising a measurement tool adapted and configured to determine a characteristic of a caudal facet joint prosthesis, the tool comprising a stem element and a trial caudal bearing surface element, the system further comprising a measurement tool holder adapted and configured to hold the measurement tool and to provide measurement of an angle between the stem element and the trial caudal bearing surface element.

2. The measurement system of claim 1 wherein a measurement surface of the measurement tool holder is adapted and configured to permit measurement of an angle in a horizontal plane between the stem element and the caudal bearing surface element of the caudal facet joint prosthesis measurement tool.

3. The measurement system of claim 1 wherein a measurement surface of the measurement tool holder is adapted and configured to permit measurement of an angle in a median plane between the stem element and the caudal bearing surface element of the caudal facet joint prosthesis measurement tool.

4. The measurement system of claim 1 wherein the measurement tool further comprises a fixed connection element positioned between the stem element and the trial caudal bearing surface element.

5. The measurement system of claim 1 wherein the measurement tool further comprises a moveable connection element positioned between the stem element and the trial caudal bearing surface element.

6. The measurement system of claim 1 wherein the measurement tool further comprises a lockable connection element positioned between the stem element and the trial caudal bearing surface element.

7. The measurement system of claim 1 wherein the measurement tool further comprises a polyaxial connection element positioned between the stem element and the trial caudal bearing surface element.

8. The measurement system of claim 1 wherein the measurement tool further comprises a lockable polyaxial connection element positioned between the stem element and the trial caudal bearing surface element.

9. The measurement system of claim 1 wherein the measurement tool comprises a radiopaque element.

10. The measurement system of claim 1 wherein the trial caudal bearing surface element is adapted and configured to replicate a target anatomical surface.

11. The measurement system of claim 1 wherein the trial caudal bearing surface element is adapted and configured to predict the location of a target anatomical position of an implanted element.

12. The measurement system of claim 11 wherein the trial caudal bearing surface element is adapted and configured to duplicate a target anatomical position of the implanted element.

13. A facet joint prosthesis measurement tool holder comprising a measurement surface connected to a holder element adapted and configured to hold a facet joint prosthesis measurement tool, wherein the measurement surface comprises two plates, the plates being at right angles to each other.

14. A facet joint prosthesis measurement tool holder comprising a measurement surface connected to a holder element adapted and configured to hold a facet joint prosthesis measurement tool, wherein the holder element is adapted and configured to permit measurement of an angle between a stem element and a caudal bearing surface element of the facet joint prosthesis measurement tool.

15. The measurement tool holder of claim 14 wherein the measurement surface is adapted and configured to permit measurement of an angle in a horizontal plane between the stem element and the caudal bearing surface element of the caudal facet joint prosthesis measurement tool.

16. The measurement tool holder of claim 14 wherein the measurement surface is adapted and configured to permit measurement of an angle in a median plane between the stem element and the caudal bearing surface element of the caudal facet joint prosthesis measurement tool.

17. The measurement tool holder of claim 14 wherein the measurement tool further comprises a fixed connection element positioned between the stem element and the trial caudal bearing surface element.

18. The measurement tool holder of claim 14 wherein the measurement tool further comprises a moveable connection element positioned between the stem element and the trial caudal bearing surface element.

19. The measurement tool holder of claim 14 wherein the measurement tool further comprises a lockable connection element positioned between the stem element and the trial caudal bearing surface element.

20. The measurement tool holder of claim 14 wherein the measurement tool further comprises a polyaxial connection element positioned between the stem element and the trial caudal bearing surface element.

21. The measurement tool holder of claim 14 wherein the measurement tool further comprises a lockable polyaxial connection element positioned between the stem element and the trial caudal bearing surface element.

22. The measurement tool holder of claim 14 wherein the measurement tool comprises a radiopaque element.

23. The measurement tool holder of claim 14 wherein the trial caudal bearing surface element is adapted and configured to replicate a target anatomical surface.

24. The measurement tool holder of claim 14 wherein the trial caudal bearing surface element is adapted and configured to predict the location of a target anatomical position of an implanted element.

25. The measurement tool holder of claim 24 wherein the trial caudal bearing surface element is adapted and configured to duplicate a target anatomical position of the implanted element.

26. A facet joint prosthesis measurement tool holder comprising a measurement surface connected to a holder element adapted and configured to hold a facet joint prosthesis measurement tool, wherein the measurement surface is adapted and configured to permit measurement of an angle between a stem element and a caudal bearing surface element of the facet joint prosthesis measurement tool.

27. The measurement tool holder of claim 26 wherein the measurement surface is adapted and configured to permit measurement of an angle in a horizontal plane between the stem element and the caudal bearing surface element of the caudal facet joint prosthesis measurement tool.

28. The measurement tool holder of claim 26 wherein the measurement surface is adapted and configured to permit measurement of an angle in a median plane between the stem element and the caudal bearing surface element of the caudal facet joint prosthesis measurement tool.

29. The measurement tool holder of claim 26 wherein the measurement tool further comprises a fixed connection element positioned between the stem element and the trial caudal bearing surface element.

30. The measurement tool holder of claim 26 wherein the measurement tool further comprises a moveable connection element positioned between the stem element and the trial caudal bearing surface element.

31. The measurement tool holder of claim 26 wherein the measurement tool further comprises a lockable connection element positioned between the stem element and the trial caudal bearing surface element.

32. The measurement tool holder of claim 26 wherein the measurement tool further comprises a polyaxial connection element positioned between the stem element and the trial caudal bearing surface element.

33. The measurement tool holder of claim 26 wherein the measurement tool further comprises a lockable polyaxial connection element positioned between the stem element and the trial caudal bearing surface element.

34. The measurement tool holder of claim 26 wherein the measurement tool comprises a radiopaque element.

35. The measurement tool holder of claim 26 wherein the trial caudal bearing surface element is adapted and configured to replicate a target anatomical surface.

36. The measurement tool holder of claim 26 wherein the trial caudal bearing surface element is adapted and configured to predict the location of a target anatomical position of an implanted element.

37. The measurement tool holder of claim 36 wherein the trial caudal bearing surface element is adapted and configured to duplicate a target anatomical position of the implanted element.

38. A facet joint prosthesis measurement tool holder comprising a measurement surface connected to a holder element adapted and configured to hold a facet joint prosthesis measurement tool, wherein the measurement surface has markings to permit measurement of an angle between a stem element and a caudal bearing surface element of the facet joint prosthesis measurement tool.

* * * * *